United States Patent [19]

Werle et al.

[11] 4,389,333
[45] Jun. 21, 1983

[54] BISGUANAMINE

[75] Inventors: Peter Werle, Gelnhausen; Wolfgang Merk; Gerhard Pohl, both of Hanau; Friedhelm Hoevels, Freigericht, all of Fed. Rep. of Germany

[73] Assignee: Degussa Aktiengesellschaft, Frankfurt, Fed. Rep. of Germany

[21] Appl. No.: 346,255

[22] Filed: Feb. 5, 1982

Related U.S. Application Data

[62] Division of Ser. No. 146,247, May 5, 1980, Pat. No. 4,339,578.

[30] Foreign Application Priority Data

May 15, 1979 [DE] Fed. Rep. of Germany ....... 2919496

[51] Int. Cl.³ .................... C09K 15/16; C07D 251/18
[52] U.S. Cl. .................................. 252/401; 544/207; 568/422
[58] Field of Search .................. 252/401; 544/207; 568/440; 260/606

[56] References Cited

U.S. PATENT DOCUMENTS

| | | | |
|---|---|---|---|
| 2,237,092 | 4/1941 | Swain et al. | 23/250 |
| 2,642,409 | 6/1953 | Cordier | 544/207 X |
| 2,887,409 | 5/1959 | Van Loo | 117/139.4 |
| 3,137,736 | 6/1964 | Prinz et al. | 260/606 |
| 3,183,271 | 5/1965 | Halpern et al. | 260/606 |
| 4,208,320 | 6/1980 | Chono et al. | 544/207 X |
| 4,339,578 | 7/1982 | Werle et al. | 544/207 |

FOREIGN PATENT DOCUMENTS

| | | |
|---|---|---|
| 1768915 | 5/1972 | Fed. Rep. of Germany . |
| 1443566 | 7/1972 | Fed. Rep. of Germany . |
| 2218581 | 10/1973 | Fed. Rep. of Germany . |
| 2358856 | 5/1975 | Fed. Rep. of Germany . |
| 1577912 | 8/1969 | France . |

Primary Examiner—Brooks H. Hunt
Assistant Examiner—M. Moskowitz
Attorney, Agent, or Firm—Cushman, Darby & Cushman

[57] ABSTRACT

There are described new bisguanamines of the formula

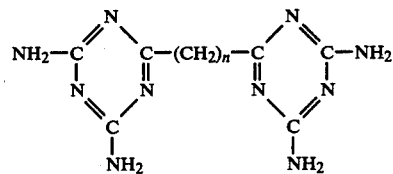

where n is a number from 10 to 20 and their production. The bisguanamines are stabilizers for formaldehyde solutions and have outstanding qualifications and action for this purpose.

19 Claims, No Drawings

BISGUANAMINE

This is a division, of application Ser. No. 146,247 filed May 5, 1980, now U.S. Pat. No. 4,339,578.

BACKGROUND OF THE INVENTION

The invention is directed to new bisguanamines and their use in the stabilization of formaldehyde solutions.

There are already known phenylene bisguanamines of the formula

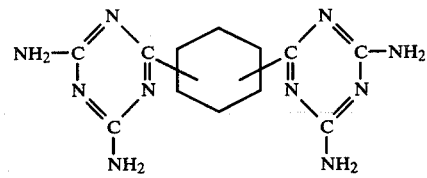

(see German AS No. 2,358,856). Besides there are known alkylene bisguanamines of the formula

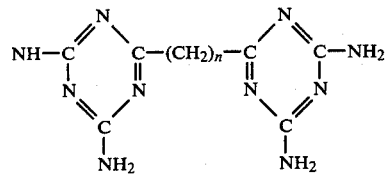

in which n is a number from 1 to 8, see Booth, Chemistry and Industry August 3, 1968, page 1047. The entire disclosure of Booth is hereby incorporated by reference and relied upon.

Aqueous formaldehyde solutions, especially solutions having a formaldehyde content above 30 weight percent are unstable if the temperatures at which they are stored fall below a certain minimum. There occurs turbidity through the formation of formaldehyde oligomers and finally the precipitation of paraformaldehyde. The higher the concentration of formaldehyde and the lower the storage temperature the more unstable are the solutions. Accordingly to the data in the monograph, "Formaldehyde" by J. F. Walker, 3rd edition, page 95, a 30 percent formaldehyde solution remains stable for up to about 3 months if it is held at at least 7° C. For a 37 percent solution the required minimum temperature is 35° C., for a 45% solution 55° C. and for a 50% solution 65° C. However, a disadvantage of the use of higher storage temperatures is that formic acid forms to a considerable extent in the formaldehyde solutions. This causes corrosion and is particularly disturbing in the use of formaldehyde solutions for condensation reactions.

The above mentioned values refer to formaldehyde solutions which contain less than 1 weight percent methanol as a stabilizer. To be sure by using higher methanol concentrations there can be produced equal storability at lower temperature, but there are required disproportionately high methanol concentrations. For example there is needed in a 37 percent formaldehyde solution for a storage temperature of 21° C., a methanol content of 7%, for 7° C. a methanol content of 10% and for 6° C. a methanol content of 12%. The addition of methanol, however considerably increases the cost of the formaldehyde solutions, especially since the methanol is generally lost in using the solutions. Apart therefrom through the methanol the speed of reaction in numerous condensation reactions, for example in the condensation with melamine, is reduced.

Besides methanol there are known as stabilizers (for formaldehyde), ethanol, propanol-1, propanol-2, ethylene glycol, glycerine, urea, methyl urea, dimethyl urea, thiourea, diethyl thiourea, formamide, melamine, methylol melamine and acetoxime (J. F. Walker, Formaldehyde", third edition, page 95, U.S. Pat. No. 2,000,152 , U.S. Pat. 2,002,243 and Swain U.S. Pat. No. 2,237,092). However, these materials must be used in concentrations of at least 2% to be effective.

Stabilizing agents which can be used in lower concentrations are for example ether, acetals of polyhydric alcohols such as pentaerythritol, sorbitol and polyethylene glycol, esters of these polyhydric alcohols and higher fatty acids, higher alcohols such as heptanol, octanol, decanol, hydroquinone, polyvinyl alcohol, its esters and acetals (Halpern U.S. Pat. No. 3,183,271; British patent 1,129,507 Japanese Pat. No. 30-3396. However, a disadvantage is that the activity of these materials is insufficient at lower concentrations and temperatures.

Furthermore, it is known to add as stabilizers lipophilic colloids such as polyoxyethylene lauryl ether (HLB (hydrophilic, lipophilic balance)-value=9.5), lipophilic sorbital esters of higher fatty acids such as sorbitol monolaurate (HLB value=8.6) or soluble or partially soluble hydrophilic colloids such as methyl cellulose, hydroxypropyl methyl cellulose, ethyl cellulose, gelatin, pectin and cellulose acetostearate. They are used in concentrations below 0.1% or below 0.5% (German OS 1443566, Prinz U.S. Pat. No. 3,137,736). Also in these cases the stabilizing action in formaldehyde solutions having a methanol content below 1% at low temperatures is not sufficient.

There also have been used as stabilizers 2,4-diaminotriazine (1,3,5) or its methylol derivatives which contain in the 6-position an aliphatic residue having 7 to 9 carbon atoms or an alkoxy or an alkylmercapto group having 5 to 10 carbon atoms (Bornmann German Pat. No. 1205073 and Belgian Pat. No. 719245). Bornmann shows that alkyl guanamines having an alkyl chain length of below 7 carbon atoms or above 9 carbon atoms are poorer stabilizers than those with 7 to 9 carbon atoms. The stabilizer effect goes down even further as the alkyl group increases from 11 to 15 carbon atoms. For a good stabilizing effect the concentration of the added aminotriazine must be 0.05 to 0.2%.

There have also been employed for stabilizing formaldehyde solutions, mixtures of guanamines, for example butyroguanamine, benzoguanamine, acetoguanamine and their methylol derivatices with fatty acid esters, ethers or acetals of a polyhydric alcohol, hydroquinone, polyvinyl alcohol as well as esters or acetals of polyvinyl alcohol. In these mixtures the guanamine must be used in concentrations of 0.08%, especially of 0.1% if a sufficient activity is to be attained (Matsuora, German AS 1219464).

Besides it is known to use as stabilizers methoxymethyl, ethoxymethyl, propoxymethyl and butoxymethyl derivatives of aceto-, propio-, butyro- and benzoguanamines which are mixed with reaction products of formaldehyde with ethylene glycol, propylene glycol, polyethylene glycol, polypropylene glycol, glycerine, trimethylolpropane, pentaerythritol, sorbitol or polyvinyl alcohol and with aceto-, propio-, butyroor benzoguanamine or with methyl-, ethyl-, propyl-, butyl-, cyclohexyl-, benzyl- or phenyl melamine (Ishizuka German AS 12268608). The concentrations in which the various guanamines or their mixtures are employed lie between 0.0025 and 0.06%. However, at these low stabilizers concentrations an elevated storage temperature is required if there is to be produced a sufficient stability of the formaldehyde solutions. If higher concentrations, namely 0.001 to 0.1% of the guanamine are used with 0.1 to 1.0% of melamine (Dakli German Pat. No. 1768915) it is true that the stabilization is better but the reactibility of the formaldehyde for condensation is reduced considerably.

It is also known that the activity of the guanamines or their methylol derivatives can be increased if there are additionally used hydrophilic polyglycol ethers of fatty alcohols or of partial esters of polyhydric alchols with fatty acids or ion-active surface active substances such as phosphoric acid esters of nonylphenyl polyethylene glycols. However, also in these cases the activity is still not satisfactory.

Finally there is also known the employing of phenylene bisguanamine as stabilizer (Diem, German As No. 2358856). This material it is true shows a better activity, however, it is relatively difficulty accessible and particularly exhibits the disadvantage that it is very difficultly soluble. Therefore it is difficult and requires much time to bring the necessary amount of stabilizer into soluble form. The alkylene bisguanamines (II) are to be sure considerably easier to dissolve, but they have either no stabilizing effect or only very small stabilizing effect.

SUMMARY OF THE INVENTION

There have now been found alkylene bisguanamines of the formula

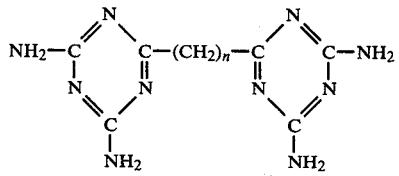    III where n is a number from 10 to 20. Thus n can be 10, 11, 12, 14, 16, 18 or 20 for example.

The alkylene bisguanamines of the invention can be produced in the same way as the known alkylene bisguanamines (II), for example by reaction of the corresponding aliphatic dinitrile with dicyandiamide in a polar solvent such as dimethyl sulfoxide, corresponding to the process in Booth, Chemistry and Industry 1968, page 1047.

For example for the production of dodecanobisguanamine there is employed 1,10-dicyanodecane, for the production of hexadecanobisguanamine there is employed 1,14-dicyanotetradecane, for the production of octadecanobisguanamine there is employed 1,16-dicyanohexadecane, for the production of eicosanobisguanamine there is employed 1,18-dicyanooctadecane and for the production of decanobisguanamine there is employed 1,8-dicyanooctane.

Furthermore there has now been found a process for the stabilization of formaldehyde solutions, those having a methanol content of less than 1% being preferred, using bisguanamines as stabilizers wherein there are employed as stabilizers the alkylene bisguanamines (III) of the invention. While the known alkylene bisguanamines (II) are unsuited for this purpose, the compounds (III) of the invention act produce outstanding stabilization. In contrast to phenylene bisguanamine (I) they have the particular advantage that they are considerably more readily soluble and therefore much easier to use.

According to the invention there are preferably employed as stabilizers the alkylene bisguanamines of formula III in which n is a number from 10 to 16, especially a number from 14 to 16.

The amount of the stabilizer to add to the formaldehyde solution depends in a given case to a certain degree on the formaldehyde content and the storage temperature of the solutions. In most cases there is employed a stabilizer content between 0.001 and 0.5 weight percent. Preferably there are chosen stabilizer contents between 0.005 and 0.10, particularly between 0.01 and 0.03 weight percent.

Unless otherwise indicated all parts and percentages are by weight.

The process can comprise, consist essentially of or consists of the steps set forth and the compositions can comprise, consist essentially of or consist of the materials set forth.

DESCRIPTION OF THE PREFERRED EMBODIMENTS (a) Production of the Alkylene Bisguanamine

EXAMPLE 1

There were dissolved in 500 ml of dimethyl sulfoxide 210 grams (2.5 moles) of dicyandiamide, which hereby was warmed to 60° C. There were introduced into this solution 192 grams (1.0 mole) of 1,10-dicyanodecane and then there were added 30 grams of a 50% aqueous potassium hydroxide solution. The mixture was heated to 135° C., held at this temperature for 45 minutes, then cooled to 100° C. and finally diluted to double its volume through the addition of 500 ml of water. There was separated from the warm mixture the precipitated dodecano-bisguanamine. It was washed with water and recrystallized from dimethyl sulfoxide. The yield was 346 grams, corresponding to 96% based on the 1,10-dicanodecane employed. The dodecanobisguanamine had a melting point of 290° C. The elemented analysis was

|  | C | H | N |
|---|---|---|---|
| found | 53.0 | 8.0 | 38.7 |
| calculates as $C_{16}H_{28}N_{10}$ | 53.3 | 7.8 | 38.9 |

The dodecanobisguanamine was identified by IR and NMR spectroscopically and also mass spectrographically.

EXAMPLE 2

The procesure was the same as in Example 1 but there was reacted 1,11-dicyanoundecane to form tridecanobisguanamine. Melting point of the guanamine: 219° C. Elemental analysis:

|  | C | H | N |
|---|---|---|---|
| found | 55.0 | 7.6 | 37.3 |
| calculated as |  |  |  |

|  | C | H | N |
|---|---|---|---|
| $C_{17}H_{30}N_{10}$ | 54.5 | 8.0 | 37.5 |

EXAMPLE 3

The procedure was the same as in Example 1 but there was reacted 1,12-dicanododecane to form tetradecanobisguanamine. Melting point of the guanamine: 180° C. Elemental analysis:

|  | C | H | N |
|---|---|---|---|
| found | 56.7 | 8.5 | 34.5 |
| calculated as $C_{18}H_{32}N_{10}$ | 56.8 | 8.5 | 35.7 |

EXAMPLE 4

The procedure was the same as in Example 1 but there was reacted 1,4-dicyanotetradecane to form hexadecanobisquanamine. Melting point of the guanamine: 219° C.
Elemental analysis:

|  | C | H | N |
|---|---|---|---|
| found | 58.5 | 8.5 | 32.8 |
| calculated as $C_{20}H_{36}N_{10}$ | 57.7 | 8.7 | 33.6 |

EXAMPLE 5

The procedure was the same as in Example 1 but there was reacted 1,16-dicyanohexadecane to form octadecanobisguanamine. Melting point of the quanamine: 230° C. Elemental analysis:

|  | C | H | N |
|---|---|---|---|
| found | 59.2 | 9.1 | 31.7 |
| calculated as $C_{22}H_{40}N_{10}$ | 59.4 | 9.1 | 31.5 |

(B) Stabilization of the Formaldehyde Solutions

There were used formaldehyde solutions with differing contents of formaldehyde and methanol. To these solutions there were added different amounts of bisguanamines as stabilizers and there was examined how long these solutions were stable at a specific storage temperature.

To dissolve the stabilizers in the formaldehyde solutions these were held in each case at 50° C. with stirring for 20 to 30 minutes.

The results are collected in the following tables. The stabilizers, the bisguanamines, are designated by n, the number of methylene groups according to formula III. The stabilizer contents are given in weight percents based on the total formaldehyde solution. As storability there was considered the time in which the solution was stable. The solutions were regarded as stable until there occurred the first separation just detectable by the eye.

TABLE 1

Solutions containing 37 weight percent formaldehyde and 0.30 weight percent methanol; pH 4.2.

| Nr. | Stabilizer Type n | Stabilizer Content % | Storage Temp. °C. | Storability Days |
|---|---|---|---|---|
| 1 | 10 | 0.020 | 0 | 20 |
| 2 | 10 | 0.030 | 0 | >120 |
| 3 | 11 | 0.020 | 0 | 30 |
| 4 | 12 | 0.020 | 0 | >90 |
| 5 | 12 | 0.030 | 0 | >120 |
| 6 | 14 | 0.010 | 0 | >120 |
| 7 | 16 | 0.005 | 0 | 10 |
| 8 | 16 | 0.010 | 0 | >120 |

TABLE 2

Solutions containing 40 weight percent formaldehyde and 0.40 weight percent methanol; pH 4.1

| Nr | Stabilizer Type n | Stabilizer Content % | Storage Temp. °C. | Storability Days |
|---|---|---|---|---|
| 9 | 10 | 0.020 | 10 | 70 |
| 10 | 10 | 0.030 | 10 | >120 |
| 11 | 11 | 0.020 | 10 | >120 |
| 12 | 12 | 0.020 | 10 | >120 |
| 13 | 12 | 0.010 | 0 | 5 |
| 14 | 14 | 0.010 | 10 | >120 |
| 15 | 16 | 0.010 | 0 | 7 |
| 16 | 16 | 0.010 | 10 | >120 |

TABLE 3

Solutions containing 44 weight percent formaldehyde and 0.45 weight percent methanol; pH 3.9.

| Nr | Stabilizer Type n | Stabilizer Content % | Storage Temp. °C. | Storability Days |
|---|---|---|---|---|
| 17 | 10 | 0.010 | 25 | 2 |
| 18 | 10 | 0.015 | 25 | >60 |
| 19 | 11 | 0.015 | 25 | >60 |
| 20 | 12 | 0.010 | 25 | 19 |
| 21 | 12 | 0.015 | 25 | >60 |
| 22 | 14 | 0.010 | 25 | >60 |
| 22 | 16 | 0.010 | 25 | >60 |

The entire disclosure of German Priorty application No. P 2919496.5 is hereby incorporated by reference.

What is claimed is:

1. An aqueous formaldehyde solution containing a stabilizing effective amount of an alkylene bisguanamine of the formula $$NH_2-C\underset{N}{\overset{N}{\underset{\|}{\diagup}}}C-(CH_2)_n-C\underset{N}{\overset{N}{\underset{\|}{\diagup}}}C-NH_2$$
$$\underset{NH_2}{\overset{}{|}} \quad \underset{NH_2}{\overset{}{|}}$$

where n is an integer of 10 to 20.

2. An aqueous formaldehyde solution according to claim 1 wherein n is 10 to 16.

3. An aqueous formaldehyde solution according to claim 2 wherein n is 14 to 16.

4. An aqueous formaldehyde solution according to claim 1 containing methanol.

5. An aqueous formaldehyde solution according to claim 4 wherein the methanol content is less than 1 weight percent.

6. An aqueous formaldehyde solution according to claim 5 wherein the methanol content is 0.30 to 0.45 weight percent.

7. An aqueous formaldehyde solution according to claim 6 wherein the methanol content is 0.30 weight percent.

8. An aqueous formaldehyde solution according to claim 1 wherein the alkylene bisguanamine is employed in an amount of 0.001 to 0.5 weight percent.

9. An aqueous formaldehyde solution according to claim 8 containing methanol, the amount of methanol being less than 1 weight percent.

10. An aqueous formaldehyde solution according to claim 9 wherein the amount of methanol is at least 0.30 weight percent.

11. An aqueous formaldehyde solution according to claim 9 wherein n is 14 to 16.

12. An aqueous formaldehyde solution according to claim 8 wherein the alkylene bisguanamine is employed in an amount of 0.005 to 0.1 weight percent.

13. An aqueous formaldehyde solution according to claim 12 containing methanol, the amount of methanol being less than 1 weight percent.

14. An aqueous formaldehyde solution according to claim 12 wherein the alkylene bisguanamine is employed in an amount of 0.01 to 0.3 weight percent.

15. An aqueous formaldehyde solution according to claim 14 containing methanol, the amount of methanol being less than 1 weight percent.

16. An aqueous formaldehyde solution according to claim 15 wherein n is 14 to 16.

17. An aqueous formaldehyde solution according to claim 15 wherein the amount of bisguanamine is 0.01 weight percent.

18. An aqueous formaldehyde solution according to claim 8 containing 30 to 50 weight percent formaldehyde.

19. An aqueous formaldehyde solution according to claim 18 containing methanol, the amount of methanol being less than 1 weight percent.

* * * * *